United States Patent [19]

Jorgensen et al.

[11] 4,111,054

[45] Sep. 5, 1978

[54] GRAVIDITY DETECTION METHOD AND APPARATUS

[75] Inventors: Hans G. Jorgensen; B. Wendell Hautaniemi, both of Ithaca, N.Y.

[73] Assignee: Ithaco, Incorporated, Ithaca, N.Y.

[21] Appl. No.: 826,556

[22] Filed: Aug. 22, 1977

[51] Int. Cl.² ............................................. G01N 29/00
[52] U.S. Cl. .......................................... 73/611; 73/614
[58] Field of Search .................. 73/611, 614, 631, 610

[56] References Cited

U.S. PATENT DOCUMENTS

| 3,164,007 | 1/1965 | Stebbins et al. | 73/611 |
| 3,423,992 | 1/1969 | Dory | 73/611 |

Primary Examiner—James J. Gill
Attorney, Agent, or Firm—Richard G. Stephens

[57] ABSTRACT

Ultrasonic detection of early pregnancy in sows and like animals is enhanced by basing an assumption of pregnancy upon detection of a substantially echo-free animal zone of predetermined width or greater which may occur over a substantial range of animal depths, combined with detection of a distinct echo from a greater depth than the echo-free zone.

10 Claims, 7 Drawing Figures

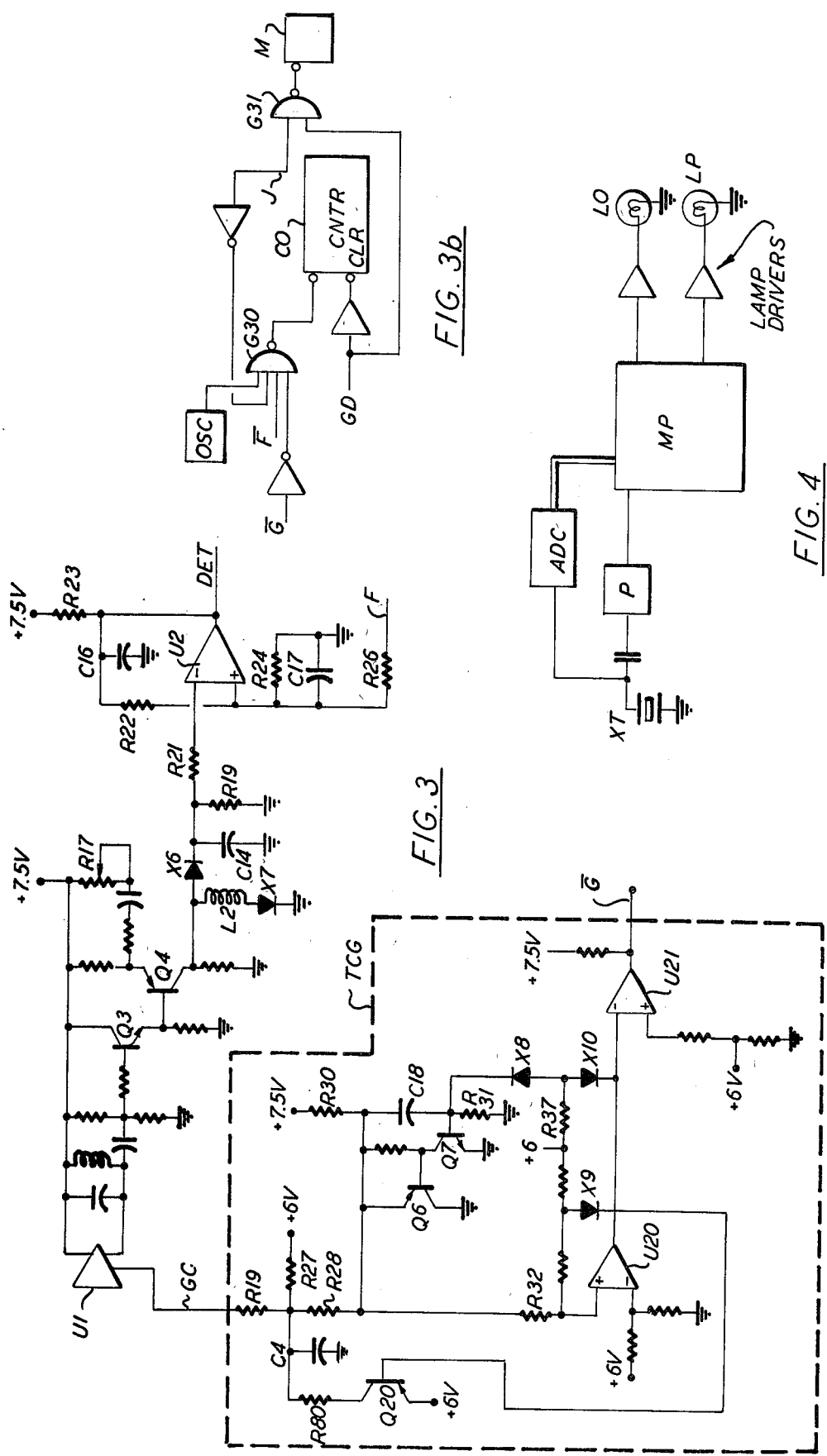

GRAVIDITY DETECTION METHOD AND APPARATUS

This invention relates to detection of pregnancy in sows and like animals early in the gestation period, and more particularly, to improved ultrasonic pregnancy detection method and apparatus which are readily usable by unskilled operators to detect early pregnancy in a more foolproof or reliable manner. Early detection of a gravid condition, say within 15 to 45 days after mating, can be of substantial economic importance to a hog breeder. It will allow non-pregnant sow to be promptly culled for slaughter, thereby saving feed costs.

The use of ultrasonic apparatus for detecting pregnancy is well known, and one form of device useful for such a purpose is shown in our prior U.S. Pat. No. 3,964,297, although that device has wider utility than pregnancy detection and is often used to determine the thickness of animal fat layers and the like, for selective breeding purposes. When the probe or transducer of that device is placed against the flank of a sow which may or may not be in the early stages of a pregnancy, the pattern of illuminated and unilluminated lights appearing on the display of that device will indicate the presence and location of density changes within the animal, and will afford a rather reliable indication of whether the animal is pregnant to an operator having experience in interpreting such displays. However, it is desirable that such detection not require an experienced operator, but fall within the capability of unskilled labor, and one object of the present invention is to provide improved ultrasonic pregnancy detection method and apparatus having a simpler form of display, preferably of a go, no-go type, readily interpretable by unskilled operators.

The broad idea of providing a simple go, no-go type of display, wherein pregnancy or the absence thereof is indicated simply by the illumination or non-illumination of one or two lights, or the operation or non-operation of a buzzer or bell, is not per se new. However, previous devices of that nature of which we are aware suffer from several defects affecting their reliability or accuracy which the present invention is intended to overcome. Thus another object of the invention is to provide improved ultrasonic pregnancy detection method and apparatus having a simple go, no-go type of indicator which is also more accurate and reliable than prior devices.

The device shown in our prior patent is provided with an operator-controllable gain control adjustment knob. While such an adjustment extends the utility of that device when the device is used by a knowledgeable operator, it is desirable that no operator adjustments be required when pregnancy detection is to be done by persons having little or no experience with ultrasonics or test instruments, and another object of the invention is to provide improved ultrasonic pregnancy testing method and apparatus wherein no such adjustments are necessary.

Shortly after the onset of pregnancy, one of the uterine horns of a sow first enlarges and becomes liquid filled, and then the uterus itself enlarges and displaces within the animal. Like prior methods and devices, the present invention depends upon detecting the presence of a fluid-filled uterine horn or uterus in order to detect early pregnancy. In a non-pregnant sow, one or more gas and food-filled intestines will normally lie against the flank. The intestines, gas and food lying against the flank of a non-pregnant animal provide numerous density changes for ultrasonic pulses transmitted into the animal, resulting in many ultrasonic echoes, as well as substantial attenuation of ultrasonic energy. Under ideal detection conditions the food, gas and intestines cause echoes to occur at numerous closely spaced depth locations, from the exterior surface to a depth of several inches inside the animal, with few if any echoes usually being detected further inside the animal due to the great acoustic attenuation which food and gas tend to cause. The innermost echoes which are detected tend to appear and disappear due to peristalsis. When a sow becomes pregnant its uterus initially becomes liquid filled and heavy, and it sinks from its normal position above the intestines, displacing the intestines so that it instead of the intestines lies against the flank. During the early stages of pregnancy when the descended uterus is liquid-filled it comprises a body of substantially uniform density, so that very few or very small reflections occur as ultrasound passes through the liquid, though distinct echoes are caused at the walls of the uterus on opposite sides of the liquid. As has been known, the problem of providing reliable detection of early pregnancy generally becomes one of determining the existence or absence of a uterine zone within the animal having an absence of appreciable echoes and less ultrasonic attenuation than surrounding portions of the animal.

In one known form of apparatus echoes received during a period of about 35 microseconds following a transmitted burst are ignored, which amounts to ignoring echoes from the external skin surface to a depth of about 1.0 inch inside the animal, but then echoes occurring during a following 40 microsecond period are noted, to determine whether a reflection occurs within a zone lying 1 to 2.1 inches inside the animal. An assumption is made that if the animal is pregnant, a liquid-filled uterus should extend throughout the second zone and that no echo should be detected during the 40 microsecond period. If an echo is detected during that period, a condition of "not pregnant" is indicated. If no echo is received during that period, a conditional determination is made that pregnancy exists. The determination is conditional because failure to receive an echo during that period can result from inadequate transducer contact or coupling rather than from presence of a liquid-filled uterus. But if an echo is detected during a third period following the 40 microsecond period, proper transducer contact tends to be assured, and thus detection of an echo during the third period after no echo was received during the 40 microsecond period is used to indicate pregnancy. The sensitivity with which echoes are detected is maintained substantially constant during the 40 microsecond period and the following third period. This prior method of detection will be seen to assume that a liquid-filled uterus extends throughout a predetermined depth zone, (the 1-inch to 2.1 inch depth zone) within the animal. While that may be the case with some pregnant sows and indeed may be the case for many pregnant sows at various time, that assumption has been found to result in significant detection errors. For example, if a pregnant animal has as appreciable layer of fat, the presence of the fat layer may displace the outer wall of the uterus into the zone in which an echo should not be received, so that the prior device will erroneously depict a fat pregnant sow as being not pregnant. A primary object of the present invention is to provide improved pregnancy detection method and apparatus wherein detection of a liquid-filled uterus of a given size or greater is made to occur no matter where the uterus lies over a substantial range of depths within the animal.

In accordance with one important aspect of the present invention, the abovementioned problem is overcome to a substantial degree by method and apparatus which operate upon the principle of examining an echo train to detect an "echo-free" gap of a certain width or greater in the train, no matter, within limits, where the gap occurs in the train. The term "echo-free" is used slightly loosely, of course, and a portion of a train may be deemed "echo-free" if it contains only echoes having very small amplitudes.

We have found that more reliable detection of hog pregnancy can be achieved by not only detecting an echo-free gap in such a manner, but by also varying the receiver detection sensitivity in a particular manner during the reception interval following each transmitted ultrasonic pulse burst. In a preferred embodiment of the invention, we effectively disable the receiver, i.e. ignore received echoes, for a first period (e.g. 14 microseconds) following transmission which causes strong echoes occurring from the animal skin layers to be ignored, and then we enable the receiver. However, as soon as we enable the receiver with a first value of gain, we then increase gain or sensitivity very substantially in a gradual manner during the remainder of a reception interval. The initial or first value of gain, being much lower than the gain established later during the reception interval, amounts to deliberately suppressing the signals received early during the reception interval to insure that tests made further inside the animal are valid. This arrangement tends to insure that a sow will not be erroneously depicted as not pregnant when the problem is really poor transducer contact, a problem which tends to occur with the mentioned prior device. While the prior device could use decreased gain to avoid that problem, then it would have difficulty detecting the inner wall of a liquid-filled uterus, which wall sometimes may lie 8 or 9 inches inside the animal. Thus another object of the invention is to provide improved pregnancy detection apparatus having an improved time-controlled gain which provides more reliable pregnancy detection.

Other objects of the invention will in part be obvious and will in part appear hereinafter.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

For a fuller understanding of the nature and objects of the invention reference should be had to the following detailed description taken in connection with the accompanying drawings, in which:

FIG. 3 is an electrical schematic diagram illustrating several portions of FIG. 1 in greater detail.

Figure 1:
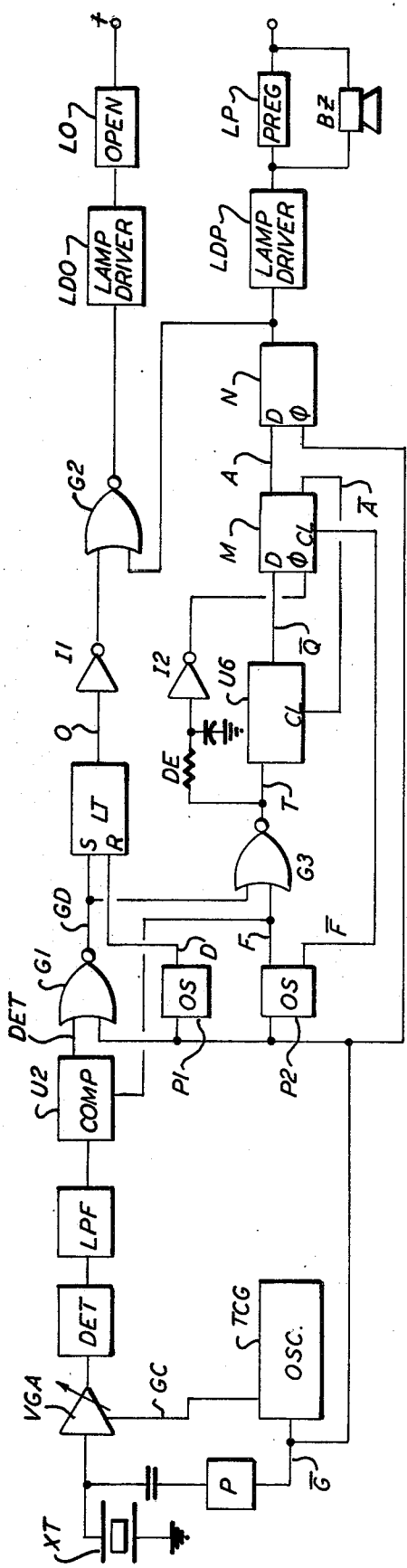
FIG. 1 is a schematic diagram, partly in block form, illustrating one form of the present invention.

FIG. 3b schematically illustrated one possible modification to the system of FIG. 1.

FIG. 4 is a block diagram illustrating alternative apparatus which may be used to practice the method of the invention.

Like the device shown in our prior patent, the pregnancy detection apparatus of the present invention is intended to be small, light and battery-powered, so as to be readily portable. It includes a piezoelectric crystal transducer on the end of a length of coaxial cable, and the operator checks the pregnancy of an animal by pressing the transducer against one flank or the other of the animal, to direct bursts of ultrasonic energy toward the uterine-zone of the animal. As will be seen below, when the animal is determined by the system to be pregnant or not pregnant, a "Pregnant" light, or an "Open" light will be lit, respectively, but in cases where the transducer is not making proper contact with the animal, neither of these lamps will be lit.

Figure 3A:
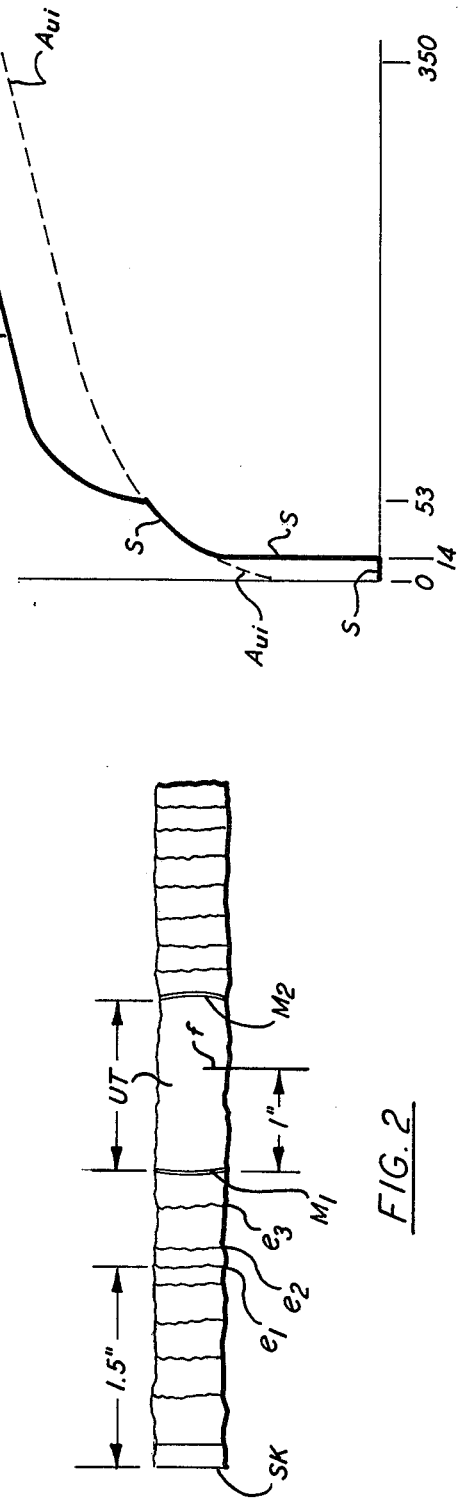
FIG. 3a is a graph illustrating a preferred gain characteristic for the system of FIG. 1.
Figure 1A:
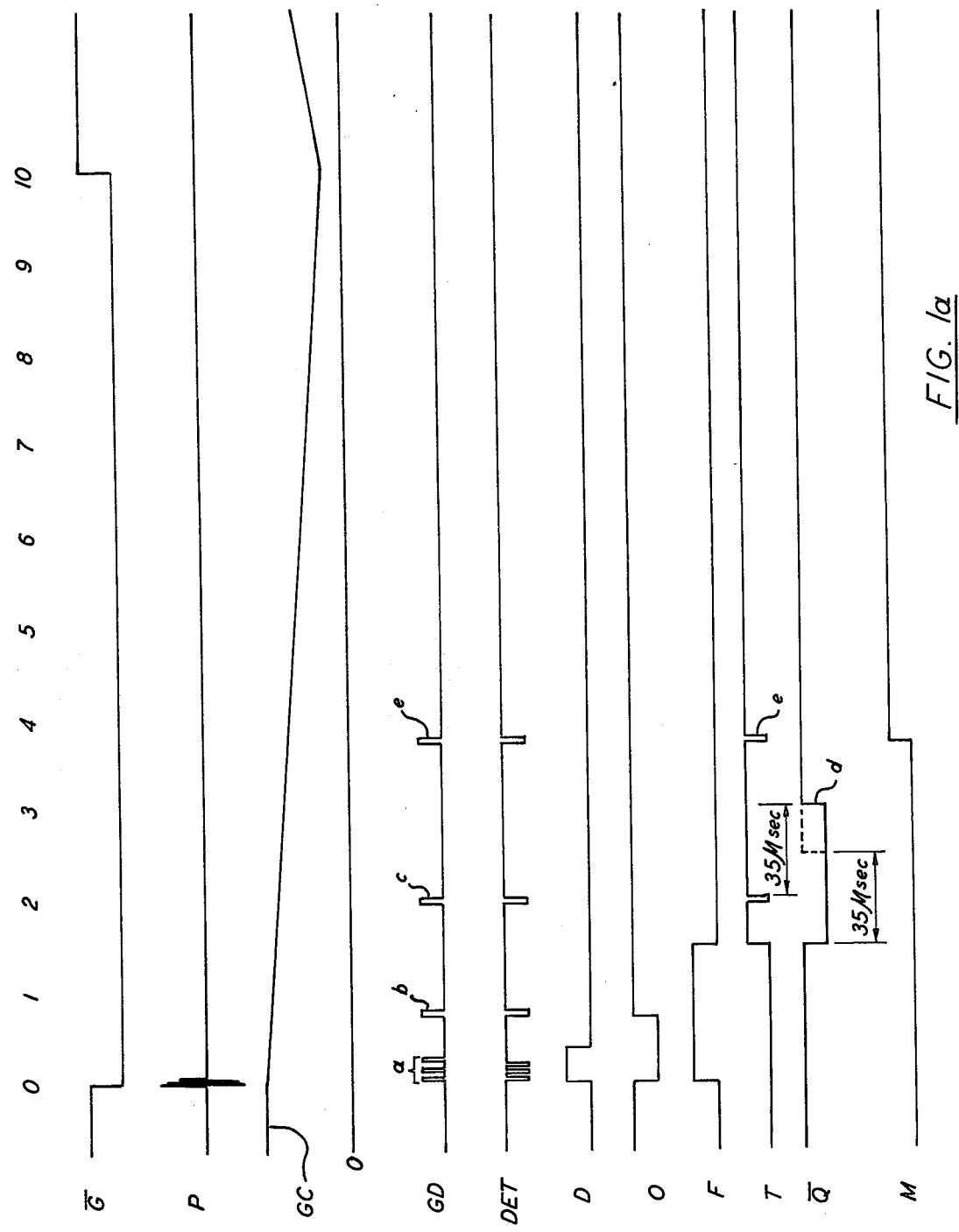
FIG. 1a is a collection of waveforms useful in understanding the operation of the device of FIG. 1.

Referring to FIG. 1, basic timing for the system is shown provided by an oscillator TCG which provides periodic low or logic zero voltage levels on line $\overline{G}$, each lower level commensing 140 times per second and lasting for approximately 350 microseconds in a typical embodiment. Each fall of line $\overline{G}$ fires pulser P which applies a large "transmit" voltage pulse to piezoelectric crystal transducer XT, causing the transducer to oscillate for several cycles at a high frequency (e.g. 1.5 megahertz), with a rapidly decaying oscillation. Line P in FIG. 1a shows the transducer pulses occurring at each transmission time. A variety of suitable pulser circuits capable of exciting the transducer are known in the art, such as SCR circuits which turn on to apply a substantial voltage pulse to such a transducer. To suitably operate such a transducer in this application it is necessary to provide a low-current high-voltage supply, having a voltage much higher than the small voltage (e.g. 7.5 volts) it is convenient to use for amplifier and logic circuits, and the device shown in FIG. 1 incorporates a DC-DC converter operated by a low-voltage battery to provide the high-voltage supply. A variety of suitable forms of converter circuits are well known, so no such converter is shown in FIG. 1. upon each application of a high voltage pulse to the transducer, the several-cycle burst of ultrasonic energy from the transducer passes into the animal, and during the remainder of the 350 microsecond interval, which may be termed the reception interval, reflected ultrasonic energy received by the transducer during that interval generates echo signals, which are applied to a variable-gain amplifier VGA. The transducer is coupled to amplifier VGA in conventional fashion. Resistance and limiter diodes (not shown) may be used between the transducer and the amplifier to prevent the firing pulse and large initial echoes emanating from the animal hide from damaging or saturating the amplifier, all in accordance with known technique. During the reception interval, and particularly during an initial portion of that interval, the gain of amplifier VGA is increased by means of a gain control voltage applied to amplifier VGA on line GC from the TCG oscillator. One suitable form which circuit TCG may take and the manner in which it may provide a voltage to control a voltage-controlled variable-gain amplifier circuit are shown in FIG. 3 and described below. The 350 approximately microsecond reception interval represents approximately the time which it takes for ultrasonic energy to pass through 20 inches of animal matter, and hence any echo received at about the end of the 350 microsecond interval will have been caused by a density change located approximately 10 inches from the surface where the transducer is coupled to the animal. The waveform on line $\overline{G}$ is shown at $\overline{G}$ in FIG. 1a for the reception interval, and the variation of the gain of amplifier VGA during the reception interval approximates the curve shown by dashed line at $A_{u1}$ in FIG. 3a. It is important to note at the outset that the overall system detection sensitivity depends in part upon the gain of amplifier VGA, but is not shown controlled exclusively by the gain of amplifier VGA, instead depending in part upon a comparator threshold voltage value, as shown below. After each 350 microsecond reception interval, and over a period of approximately 6.65 milliseconds, oscillator TCG decreases the gain to a predetermined value, in preparation for a further cycle. Thus the transducer is fired approximately every 7 milliseconds, or with a repetition rate of about 140 times per second.

Any echo signals received during the reception interval are amplified by amplifier VGA and applied to a detector DET, where they are rectified to provide unidirectional voltage pulses. Either half-wave or full-wave rectification may be used. The rectified pulses are low-pass filtered by filter LPF and applied to a voltage comparator U2, which provides a low or logic 0 signal on line DET whenever the output voltage from filter LPF exceeds a threshold. The threshold at which comparator U2 operates is altered during the reception interval in a manner to be explained below. Decreasing the U2 comparator threshold will be seen to affect the overall system sensitivity, allowing a weaker echo to be detected, and hence affecting overall system sensitivity in generally the same manner as an increase in the gain of amplifier VGA. Further, as will be seen below, echoes arriving during some portions of a reception interval will be ignored, by use of logic circuits.

Each negative pulse provided by comparator U2 on line DET during a reception interval is applied to nor gate G1 together with the low signal on line $\overline{G}$, and hence output line GD of gate G1 will rise to a logic 1 level each time an echo signal is detected. Line GD is connected to the set input line of a latch or RS flip-flop LT, and the clear or reset input line of the latch receives the set output signal from a monostable multivibrator, or one-shot P1. One-shot P1 is triggered by the fall of line $\overline{G}$ at the beginning of each reception interval and remains set for approximately 14 microseconds thereafter. Several echoes ordinarily will arrive from the animal skin and interfaces just underneath the skin, irrespective of whether the animal is pregnant. Thus during the initial 14 microseconds of each reception interval, while echoes might be arriving from a depth of zero to 0.4 inch inside the animal, latch LT is held cleared by one-shot P1, but at anytime during the remaining 336 microseconds of a reception interval a detected echo will raise line GD to set the latch and provide a logic 1 voltage on line 0. In FIG. 1a several pulses shown at $a$ on line GD occuring while line D is high do not cause setting of latch LT, but the first echo pulse (shown at $b$ on line GD) which occurs after P1 has reset, sets latch LT, raising line O. The signal on line 0 is inverted by inverter I1 to provide a logic 0 signal to nor gate G2. Since flip-flop N will be in a cleared condition when the first such echo is detected, as will be seen below, the first detected echo will cause a logic 1 signal from gate G2 to operate lamp driver LDO, thereby to illuminate "Open" lamp LO. If, after the first detected echo sets latch LT to turn on lamp LO, flip-flop N is set sometime during the remainder of the reception interval, which will be the case if pregnancy is detected, gate G2 will turn off lamp LO. As will be shown below, if pregnancy is detected, flip-flop N will remain set constantly, not only throughout successive reception intervals but also throughout the relatively long 6.65 millisecond periods in between successive reception intervals. Thus if pregnancy is detected during each of a series of successive reception intervals, lamp LO will be lit for only a portion of the first 350 microsecond interval, and it then will remain permanently off during the further reception intervals. Such operation is much preferred to an arrangement in which lamp LO might be very briefly turned on during each reception interval, since repeated illumination of that lamp, even with an extremely low duty cycle, might be misinterpreted by the operator to represent an "on" condition, especially under low ambient light conditions. If flip-flop N is not set during the reception interval, the situation when pregnancy is not detected, lamp LO will remain on from the time latch LT is set to the end of the reception interval, and then remain on for the 6.65 millisecond interval until one-shot P1 is set clear latch LT when the next transmit pulse occurs, providing a high-percentage dutycycle for lamp LO so that its illumination is readily observable.

It may be noted that at least one echo must be detected to set latch LT after one-shot P1 has reset and line D has fallen, i.e. during the last 336 microseconds of the reception interval, or else "Open" lamp LO will not be illuminated, even in the absence of a detected pregnancy. Thus if the transducer is not properly contacting the animal, the absence of an echo to set latch LT will result in lamp LO being not lit, and the operator will be advised, by both lamps LO and LP being out, that proper transducer contact is not being made. Latch LT is cleared by one-shot P1 at the beginning of each reception interval. If, after neither lamp is lit, the operator moves the transducer to make proper contact with a non-pregnant animal, latch LT will be set sometime during the next reception interval and "Open" lamp LO will immediately turn on. It is important to note that immediately after one-shot P1 resets so that latch LT could be set by an echo, the system sensitivity is much lower than later during the reception interval. This tends to insure that latch LT will not be set very soon after P1 resets unless a quite strong reflection occurs at that time, since any such reflection occurs only a short distance (e. g. 0.5 inch) inside the animal and should be quite strong if proper transducer contact is being made.

The fall of line $\overline{G}$ at each transmit time also temporarily sets one-shot P2, for approximately 53 microseconds, or the time for echoes to be received from a depth of zero to 1.5 inches, as indicated by waveform F in FIG. 1a. The F or set output line of one-shot P2 is connected to nor gate G3, so that during that 53 microsecond interval output line T of gate G3 is low, irrespective of whether the detection of any echo pulse raises line GD, and a re-triggerable one-shot U6 remains cleared. Flip-flop M is a D-type flip-flop, and setting of that flip-flop during a reception interval indicates that pregnancy is detected. During the 53 microsecond interval while one-shot P2 is set, its complement line $\overline{F}$ holds flip-flop M cleared. Thus while one-shot P2 is set, no echo or absence of an echo can result in an indication of pregnancy. This arrangement prevents a thick layer of fat, in which few or no density changes occur, from being falsely detected as if it were a liquid-filled uterus. Such a layer of fat would have to lie 1.5 to 2.5 inches inside the animal to be falsely detected as a liquid-filled uterus, and such a position for a layer of fat is believed to be extremely unlikely.

At the end of the 53 microsecond interval as P2 resets, lowering line F, output line T of gate G3 will rise. If an echo is being detected at the instant P2 resets, line T will rise slightly later, at the trailing edge of the echo. In either case the rise of line T will trigger or set a re-triggerable one-shot U6, which may comprise, for example, a type MC 1452 8CP integrated circuit one-shot, which is provided with a predetermined set period, such as 35 microseconds, corresponding to a minimum width (1 inch for 35 microseconds) one may desire to establish as the minimum width which a liquid-filled uterus must have before one will deem pregnancy to exist in a sow. The rise of line T is also applied through a small delay DE and inverter I2 to the $\phi$ or clock line of D-type flip-flop M. Delaying the signal to line $\phi$ until after U6 has set prevents abnormal triggering of flip-flop M should an echo occur precisely when P2 is resetting and line F is going low. One-shop U6 then will remain set for 35 microseconds if no echo is detected during that time, and at the end of such a 35-microsecond period one-shop U6 would reset. The time at which U6 would reset if no echo were received after U6 was set is shown in dashed lines at waveform Q in FIG. 1a. However, if an echo is detected less than 35 microseconds after one-shot U6 was set, as is assumed in FIG. 1a, where an echo is shown causing a pulse at $c$ on line GD, the echo will cause line T to fall and then to rise. The rise of line T at the trailing edge of any such echo will re-trigger one-shot U6, with the result that U6 will not reset 35 microseconds after one-shop P2 resets, but rather 35 microseconds after the trailing edge of the echo, as is shown at $d$ in FIG. 1a. If a series of successive echoes are detected while one-shot U6 is set, with successive echoes spaced close enough together in time that no gap of at least 35 microseconds exist between adjacent pairs of such echoes, one-shot U6 will remain set throughout the remainder of the 350 microsecond reception interval, preventing flip-flop M from being set during that reception interval, and, as will be seen below, preventing "Pregnancy" lamp LP from being lit.

Conversely, once one-shot U6 has been set, if a gap of 35 microseconds or more then occurs between any adjacent or successive pair of detected echoes during the remainder of the reception interval, one-shot U6 will reset. Then, if thereafter during the remainder of the reception period, an echo is detected, such as the echo causing the pulses shown at $e$ on line GD and T in FIG. 1a, its leading edge will lower line T and, with a slight delay, raise the clock imput line $\phi$ of flip-flop M. With the output line $\overline{Q}$ of thenreset one-shot U6 high, the rise of the $\phi$ input to flip-flop M then will set that flip-flop, making a decision that pregnancy exists. The setting of flip-flop M provides logic 0 on line $\overline{A}$ to hold one-shot U6 cleared, and provides logic 1 on line A to the D input of flip-flop N, another "D-type" flip-flop. Then when line G rises at the end of the reception interval, flip-flop N will be set, operating lamp driver LDP so that "Pregnant" lamp LP will be lit, and lowering the output from gate G2, so that "Open" lamp LO will be extinguished, even though an echo will have set latch LT to turn it on some microseconds before. Flip-flop N then will remain set and thereby cause lamp LP to be lit until and unless a logic 0 exists on line A when line $\overline{G}$ goes high at the end of some subsequent reception interval. Thus lamp LP will remain constantly lit, as long as flip-flop M is set during every reception interval, and buzzer BZ operated in parallel with lamp LP will provide a steady audible signal.

If no echo is received during the remainder of the reception interval following reset of re-triggerable one-shot U6, flip-flops M and N will, of course, remain cleared, lamp LP will not be lit and lamp LO will be illuminated. Thus pregnancy will not be indicated unless an echo is received during the same reception interval after re-triggerable one-shot U6 has reset, i.e. after a "no-echo" gap of 35 microseconds has been detected. A distinct echo ordinarily will be received after U6 resets due to the reflection occurring at the inner wall of a liquid-filled uterus and flip-flops M and N will be set to indicate pregnancy. A distinct echo will be sensed even if that wall of the uterus lies for (e.g. 8 or 9 inches) inside the animal due to the high gain at the time such a reflection reaches the transducer. However, if the absence of echoes which has allowed U6 to reset was caused by severe echo attenuation due to a food and gas-filled intestine, no echo will occur after U6 has reset and a false indication of pregnancy will not occur.

It is an important feature of the invention that one-shot U6 will reset if the "echo-free" gap occurs anywhere between 1.5 and approximately 10 inches inside the animal, so that a liquid-filled uterus may be detected at a variety of different depths.

The overall detection sensitivity of the system increases throughout the 0.4 to 1.5 inch interval (14 to 53 microsecond interval) in the manner shown in FIG. 3a by reason of a varying control voltage applied to increase the gain of amplifier VGA. The overall detection sensitivity is also governed by the threshold of comparator U2. The set output line F of one-shot P2 is connected to comparator U2 in a manner shown in detail in FIG. 3, and thus during that interval, the set condition of one-shot P2, together with a fixed-bias circuit, establishes a first threshold level for comparator U2. As one-shot P2 resets at the end of the 53 microsecond interval, the fall of its output line F decreases the comparator U2 threshold, thereby increasing system detection sensitivity. As is described below in connection with FIG. 3, the step decrease in voltage on line F as one-shot P2 resets is applied to a capacitor associated with comparator U2, so that the comparator threshold decreases with the exponential decrease of a discharging capacitor, thereby increasing overall sensitivity in the manner shown at S in FIG. 3a, with an initially great slope or rate of change of sensitivity which gradually decays to a lower rate of change of sensitivity. A major increase in sensitivity will be seen to occur as echoes are being received from 1.5 to 2.5 inches inside the animal. It is generally desirable that sensitivity change gradually when one-shop P2 resets rather than changing in step fashion in order to avoid switching transients, but use of the particular time-constant shown is not essential.

Figure 2:
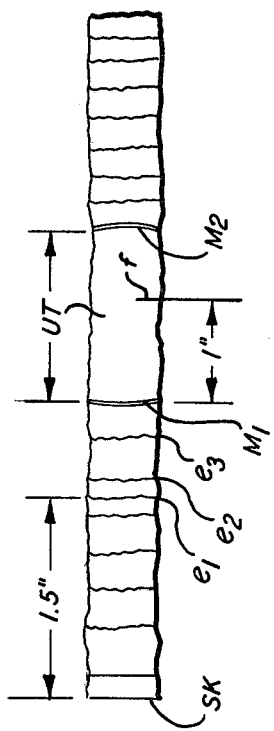
FIG. 2 is a diagram illustrating a portion of an animal, and useful in understanding the operation of the system of FIG. 1.

It now will be seen that pregnancy is assumed to be present if, along the ultrasonic energy path within the animal, more than about 1.5 inches inside the animal, a gap or "no echo" distance of one inch or more exists, which is followed by an echo at some greater distance inside the animal. In FIG. 2 a liquid-filled uterus UT is assumed to lie within an animal at a greater depth than 1.5 inches measured from the external skin surface SK or hide of the animal, and the width of the uterus exceeds 1 inch. Various animal features such as intestinal walls, muscles, food, etc., on both sides of the uterus result in density changes indicated by wavy vertical lines. It will be apparent from the above explanation that under such conditions, one-shot U6 would be set at the time an echo is received from the density change indicated at $e_1$, not because of an echo from $e_1$ but because of the 1.5 inch period selected for one-shot P2. Shortly later, echoes received from density changes at $e_2$, $e_3$, and $u_1$ (the nearer wall of the uterus) would each retrigger one-shot U6, maintaining it set. However, after the echo from wall $u_1$ is detected, no appreciable echoes would be detected for a time exceeding 35 microseconds due to the absence of density changes within the liquid-filled uterus, and one-shot U6 will reset. U6 would reset at the time at which an echo would be received from location $f$ if a density change existed at location $f$, which is assumed not to be the case. Then sometime later, when an echo is received from further wall $u_2$ of the uterus, flip-flop M will be set, and pregnancy will be indicated to exist. It is important to note that similar detection will occur if the liquid-filled uterus lies closer to the surface SK, so long as at least a 1-inch width portion of the uterus lies more than 1.5 inches from the surface, and similar detection will occur if the uterus lies further away from the surface than where shown, so long as a one-inch portion of the uterus including its inner wall lies within ten inches from the surface SK. If a liquid-filled uterus were to lie within the confines of the 1.5 inch dimension shown in FIG 2, a pregnancy detection would not occur. However, the uterus of a sow is extremely unlikely to lie so close to the animal surface. The liquid-filled uterus frequently will lie inside the sow at substantially varying distances from 1.5 to 10 inches, however, and the invention will be seen to readily detect such conditions, no matter where the uterus lies within such a range. If the uterus is less than one inch wide, a reflection from its wall $u_2$ will retrigger one-shot U6, preventing it from resetting, and an "open", or non-pregnant indication will be provided.

In the exemplary basic timing circuit TCG shown in FIG. 3 capacitor C18 is connected to be charged up through resistors R30 and R31 during each of the 6.65 millisecond periods in between successive 350 microsecond reception intervals. When the capacitor charge reaches an upper level of about +4 volts, the signal applied to the non-inverting input of comparator amplifier U20 exceeds the fixed voltage applied to the inverting input, so that the U20 output swings positive, cutting off diodes X9 and X10, and driving the output of comparator U21 negative, resulting in the fall of line $\overline{G}$, pulsing of the transducer and the beginning of the 350 microsecond reception interval. With diode X10 cut off, current flows through resistor R37 and diode X8 to turn on transistor Q7, which in turn turns on transistor Q6, discharging the capacitor C18 voltage. The capacitor C18 voltage decreases rapidly at a rate commensurate with the current through diode X8. When the capacitor voltage reaches a lower limit of about +2 volts approximately 350 microseconds later, the output of comparator U20 swings negative, which not only switches comparator U21 to provide a logic 1 signal on line $\overline{G}$, but also turn on diode X10, thereby cutting off diode X8. These events signal the end of the 350 microsecond reception interval. Capacitor C18 then charges up through resistances R30 and R31, and through resistor R28, charging more slowly than it discharged. When the capacitor voltage again reaches its upper limit, about 6.65 milliseconds later, comparator U20 switches again to provide a further transmit pulse and begin a new 350 microsecond reception interval.

During each 6.65 millisecond period the negative output of amplifier U20 maintains transistor Q20 conducting, keeping capacitor C4 charged up to +6 volts. That voltage is applied via resistor R9 to the gain control line GC of amplifier U1, providing a very low gain or in essence disabling amplifier U1. When amplifier U20 switches at the beginning of a reception interval, transistor Q20 is cut off, so that as capacitor C18 discharges during the 350 microsecond reception interval, the voltage applied on line GC decreases, increasing the gain of amplifier U1. The voltage on line GC decreases exponentially, thereby causing the gain of amplifier U1 to increase substantially in accordance with the curve plotted as $A_{u1}$ in FIG. 3a. Amplifier U1 may comprise, for example, a commercially-available Type 1350P voltage-controlled amplifier.

In FIG. 3 the U1 amplifier output is shown connected to an emitterfollower transistor Q3 through band-pass filtering, which is rather broadly tuned to embrace the transducer oscillation frequency. The output of the emitter-follower is further amplified by transistor Q4, the gain of which is shown provided to be manually adjustable by means of potentiometer R17 provided in its emitter circuit. Potentiometer R17 is an internal adjustment made at the factory, not an operator adjustment. Amplifier U1 and transistors Q3 and Q4 collectively provide the variable-gain amplication indicated at VGA in FIG. 1. The output voltage from transistor Q4 is detected by diode detector X6. Diode X7, together with RF blocking choke L2, biases detector diode X6 partly on, so that echo signals need not exceed the entire forward threshold voltage of X6 in order to be detected. Capacitor C14 and resistor R19, together with input resistor R21, form the low-pass filter circuit shown at LPF in FIG. 1.

The threshold voltage applied to the non-inverting input line of comparator amplifier U2 will be seen to depend upon a fixed bias voltage applied via resistors R23 and R22, and on the voltage on line F applied via resistor R26. During the initial 53 microseconds of a reception interval while one-shot P2 (FIG. 1) is set, the logic 1 voltage on line F, together with the fixed bias voltage establishes a first threshold level for comparator U2, but when one-shot P2 resets, line F drops to lower the threshold voltage applied to the non-inverting input line. The threshold voltage drops gradually however, as capacitor C17 discharges to a lower value through resistor R26.

While a re-triggerable one-shot has been shown as the primary element of the "no-echo" timing circuit, it is important to note that other forms of timing circuits may be substituted without departing from the invention. In FIG. 3b a digital counter substitute for one-shot U6 is shown. During each reception interval after one-shot P1 has reset, nand gate G30 connects pulses from an oscillator OSC to advance binary counter CO, but every time an echo is detected the rise of line GD causes counter CO to be reset to zero (or to another predetermined reference count), and hence counter CO will not be advanced to a count high enough to raise its output line J unless no echoes are detected for a sufficiently long period of time, the length of that period of time depending upon the frequency of the oscillator and the number of counts required to advance counter CO from its reference count to the count which raises line J. The rise of line J stops further advancement of the counter, and flip-flop M' is then later set if a succeeding echo pulse raises line GD to lower the output of nand gate G31. Flip-flop M' may control a further flip-flop such as flip-flop N in FIG. 1. Other timing functions shown in FIG. 1 such as those performed by circuit TCG and one-shots P1 and P2, may instead be performed using one or more counters without departing from the invention.

A variety of modifications may be made in the logic circuits shown in accordance with well-known principles. It will be apparent that various dimensions and time periods referred to in the above description relate to a specific embodiment designed for use with hogs and that many of the values discussed may be varied in various applications of the invention.

It is important to note that the basic method of the invention can be carried out using apparatus much different in form than that shown, by use of a digital microprocessor, for example. In FIG. 4 a conventional microprocessor MP is programmed to provide periodic output pulses to fire pulser P to excite transducer XT. Echo signals emanating from the transducer during a plurality of successive time intervals following each transmit pulse are digitized by an analog-to-digital converter ADC. Thus digital signals indicating the presence or absence of echoes, i.e. the magnitudes of such echoes, for each of say several hundred periods after a transmit pulse are provided. Microprocessor MP may be easily programmed to process the digital signal provided for each period, to perform the following operations, for example:

1. To set a first flag is an echo occurring anytime during a first group of the periods exceeds a prescribed amplitude. The prescribed amplitude needed by an echo to cause setting of the flag may be readily arranged to increase with the number of the period, and thus setting of the flag may be determined by simple comparison of successive digitized echoes with a stored list of numbers, or with a list of numbers, some of which are stored and some of which are computed.

2. To set a second flag if no echoes occur (i.e. all digitized echo signals fall below prescribed amplitudes) throughout a prescribed number of successive periods.

3. To set a third flag if any echo exceeding a prescribed amplitude is detected after the second flag has been set.

4. To test the flags at the conclusion of the periods, to provide a pregnancy indicating output signal if the third flag is set, and to provide a non-pregnancy output signal if the first flag is set and the third flag is not set.

A particular advantage of a programmed micro processor system of the nature of FIG. 4 is that the system sensitivity or gain shaping can be prescribed by simple storage of a list of numbers, which would allow ready reprogramming to accommodate different classes of animals by mere substitution of different numbers into storage, such as by use of different read-only memories with the microprocessor.

The embodiments of the invention in which an exclusive property or privilege is claimed are defined as follows:

1. Apparatus for detecting pregnancy within an animal, comprising, in combination: ultrasonic transmission and reception means for transmitting ultrasonic energy into said animal and receiving reflected energy in the form of electrical echo signal pulses occurring during a reception interval following transmission of said energy; first means for detecting the occurrence of an echo signal which occurs during said reception interval later than a first predetermined amount of time after said transmission and for providing a first logic signal upon detection of any such echo signal; second means for detecting the occurrence of each echo signal which occurs during said reception interval later than a second predetermined amount of time after said transmission, for providing a second logic signal if and when no echo signal has been detected for a third predetermined amount of time elapsed at any time during said reception interval after said second predetermined amount of time has elapsed, and for providing a third logic signal if an echo signal is detected after provision of said second logic signal; and indicating means responsive to said logic signals for providing a pregnancy indication upon occurrence of said third logic signal and for providing a non-pregnancy indication upon occurrence of said first logic signal and no occurrence of said third logic signal.

2. Apparatus according to claim 1 in which said first means is operative to detect echo signals with a sensitivity which increases after said first predetermined amount of time.

3. Apparatus according to claim 1 in which said second predetermined amount of time exceeds said first predetermined amount of time.

4. Apparatus according to claim 1 in which said second means is operative to detect echo signals with a sensitivity which increases after said second predetermined amount of time.

5. Apparatus according to claim 1 in which said second means comprises a retriggerable monostable multivibrator having a set period corresponding to said third predetermined amount of time and a reset output line for providing said second logic signal.

6. Apparatus according to claim 1 in which said indicating means comprises a non-pregnancy indicator connected to be operated by said first logic signal but disabled by occurrence of said third logic signal, and a pregnancy indicator connected to be operated upon occurrence of said third logic signal.

7. Apparatus according to claim 1 wherein said indicating means comprises a pregnancy indicator and a storage circuit, said pregnancy indicator being operable to provide a pregnancy indication while said storage circuit is set, said storage circuit being connected to be set by the first reception interval during which said third logic signal occurs and to remain set until said third logic signal has not occurred during a subsequent reception interval.

8. Apparatus according to claim 7 wherein said indicating means comprises a non-pregnancy indicator connected to be operated upon the occurrence of each of said first logic signals unless said storage circuit is set.

9. The method of indicating pregnancy within an animal which comprises the steps of: transmitting ultrasonic energy into said animal and receiving reflected energy in the form of a series of electrical echo signals occuring during a reception interval following transmission of said energy; detecting the occurrence of any echo signal which occurs during said reception interval later than a first predetermined amount of time after said transmission and providing a first logic signal upon detection of any such echo signal; detecting the occurrence of each echo signal which occurs during said reception interval later than a second predetermined amount of time after said transmission, providing a second logic signal if and when no echo signal has been detected for a third predetermined amount of time elapsed at any time during said reception interval after said second predetermined amount of time has elapsed and providing a third logic signal if an echo signal is detected after provision of said second logic signal; providing a pregnancy indication upon occurrence of said logic signal during said reception interval; and providing a non-pregnancy indication upon occurrence of said first logic signal and no occurrence of said logic signal during said reception interval.

10. The method of detecting a gap having or exceeding a predetermined time width in a train of ultrasonic echo pulses no matter where said gap may occur in said train, which comprises the steps of: applying said pulses to set a retriggerable monostable multivibrator having a set period corresponding to said predetermined width; applying said pulses to one input line of a coincidence circuit to conditionally enable said circuit during the absences of said pulses; and applying a reset signal from said multivibrator to said coincidence circuit, thereby enabling said coincidence circuit if and only if said gap occurred in said train.

* * * * *